United States Patent [19]

Kurmeier et al.

[11] 4,151,294
[45] Apr. 24, 1979

[54] ALKYNOLS AND PROCESS FOR THEIR PREPARATION

[75] Inventors: Hans-Adolf Kurmeier; Erich Schacht; Joachim Gante; Dieter Orth; Zdenek Simane; Albrecht Wild, all of Darmstadt, Fed. Rep. of Germany

[73] Assignee: Merck Patent Gesellschaft mit beschrankter Haftung, Darmstadt, Fed. Rep. of Germany

[21] Appl. No.: 805,045

[22] Filed: Jun. 9, 1977

[30] Foreign Application Priority Data

Jun. 10, 1976 [DE] Fed. Rep. of Germany ....... 2626018

[51] Int. Cl.² .............. C07C 33/06; C07C 43/28; A61K 31/35; A61K 31/085
[52] U.S. Cl. ............. 424/283; 260/345.9 R; 424/340; 424/341; 424/343; 424/345; 568/637; 568/639; 568/809; 568/811; 568/812
[58] Field of Search .......... 260/618 D, 618 E, 613 R, 260/345.9; 424/341, 283, 343, 345; 568/809, 811, 812, 637, 639

[56] References Cited

U.S. PATENT DOCUMENTS

| 3,879,449 | 4/1975 | Anderson et al. | 260/345.9 |
| 3,888,933 | 6/1975 | Anderdon | 260/618 D |
| 3,929,902 | 12/1975 | Galantay | 260/618 D |
| 3,939,278 | 2/1976 | Lacefield et al. | 424/340 |
| 3,969,415 | 7/1976 | Galantay | 260/618 D |
| 4,057,647 | 11/1977 | Gante et al. | 260/618 D |
| 4,060,633 | 11/1977 | Gante et al. | 260/613 R |

Primary Examiner—Norman Morgenstern
Attorney, Agent, or Firm—Millen & White

[57] ABSTRACT

Alkynols of the formula,

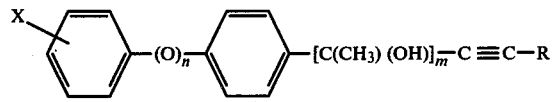

wherein X is F, Cl or Br; n is 0 or 1; m is 0 or 1 and R (if m is 0) is hydroxyalkyl of 1-6 carbon atoms or (if m is 1) alkyl, straight-chain hydroxyalkyl or straight-chain tetrahydropyran-2-yloxyalkyl of 2-6 carbon atoms in the alkyl, have anti-inflammatory activity.

17 Claims, No Drawings

ALKYNOLS AND PROCESS FOR THEIR PREPARATION

BACKGROUND OF THE INVENTION

This invention relates to novel anti-inflammatory compounds.

Alkyne compounds of the formula

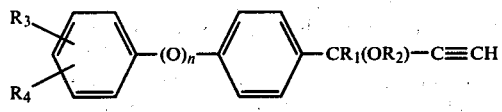

wherein $R^1$ is H, alkyl of up to 4 carbon atoms or phenyl; $R^2$ is H, aliphatic acyl of up to 6 carbon atoms or aroyl of up to 11 carbon atoms; $R^3$ and $R^4$ are H, F, Cl or Br and n is 0 or 1, are disclosed by Gante et al. in U.S. Ser. No. 697,579, filed June 18, 1976, as having anti-inflammatory activity.

Furthermore, alkyne compounds of the formula

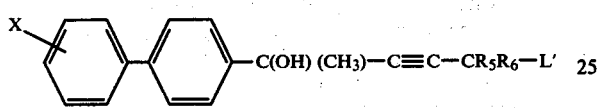

wherein X is Cl, Br or J; $R_5$ and $R_6$ each are H or alkyl with up to 3 carbon atoms; and L' is hydroxy or tetrahydropyranyl-2-oxy, are disclosed by Galantay in German Offenlegungsschrift No. 2 258 349 as being intermediates.

Finally, alkyne compounds of the formula

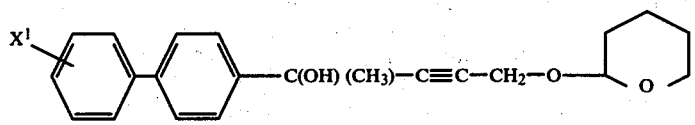

wherein $X^1$ is F, Cl or Br, are disclosed by Anderson et al. in U.S. Pat. No. 3,879,449, as intermediates.

The applications or patents cited are incorporated herein by reference.

SUMMARY OF THE INVENTION

This invention relates, in a compositional aspect to novel alkynol compounds of Formula I

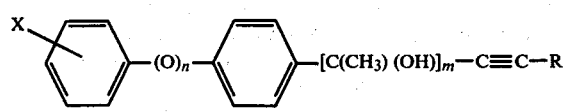

wherein X is F, Cl or Br; n is 0 or 1; m is 0 or 1 and R, when m is 0, is hydroxyalkyl of 1-6 carbon atoms or, when m is 1, is alkyl, straight-chain hydroxyalkyl or straight-chain tetrahydropyran-2-yloxyalkyl, each alkyl being of 2-6 carbon atoms.

In another compositional aspect, this invention relates to a pharmaceutical composition comprising a compound of Formula I, in admixture with a pharmaceutically acceptable carrier.

In a method of use aspect, this invention relates to a method of treating an animal afflicted with an inflammatory condition, comprising administering to the afflicted animal an anti-inflammatorily effective amount of a compound of Formula I, in admixture with a pharmaceutically acceptable carrier.

A process for preparing alkynols of Formula I comprises treating a compound of Formula II,

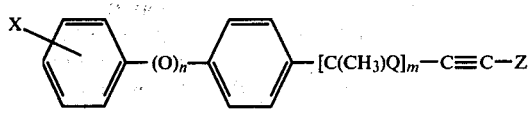

wherein Q is a functionally-modified hydroxyl and Z, if m is 0, is alkyl of 1-6 carbon atoms in the alkyl substituted by Q or, if m is 1, is alkyl or alkyl substituted by Q, each of 2-6 carbon atoms in the alkyl, and X, n and m are as above, with a solvolyzing agent and the further optional step of hydrolytically cleaving a tetrahydropyran-2-yloxy group present in the product thus obtained.

DETAILED DESCRIPTION

In the specification,

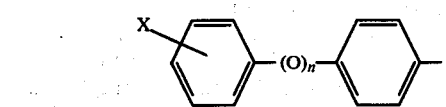

is referred to as "Ar" and

as "A".

Therefore, compounds of Formula I can alternatively be represented by either of Formula Ia a

or Formula Ib

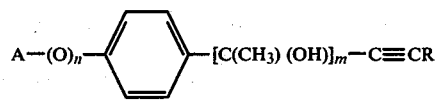

wherein A, Ar, m, n and R have the values given above.

Compounds of Formula I therefore include those wherein:

(1) X is F;
(2) X is Cl;
(3) X is Br;
(4) n is 0, including each of (1)–(3);
(5) n is 1, including each of (1)–(3);
(6) m is 0, including each of (1)–(5);
(7) m is 1, including each of (1)–(5);
(8) R is hydroxyalkyl of 1-6 carbon atoms, including each of (1)–(6);
(9) R is straight-chain hydroxyalkyl of 2-6 carbon atoms, including each of (1)–(5) and (7);

(10) R is alkyl is 2-6 carbon atoms, including each of (1)-(5) and (7); and

(11) R is straight-chain tetrahydropyranyl-2-oxyalkyl of 2-6 carbon atoms in the alkyl, including each of (1)-(5) and (7).

In compounds of Formula I, n preferably is 0. Consequently, Ar preferably is a substituted 4-biphenylyl radical. X is preferably fluorine or chlorine, preferably in the p-position, but by X can also be present in the o- or m-position.

A preferably is o- or p-fluorophenyl, o- or p-chlorophenyl; secondarily m-fluoro or m-chlorophenyl or o-, m- or p-bromophenyl.

If n is 1, Ar preferably is 4-(4-fluorophenoxy)-phenyl or 4-(4-chlorophenoxy)-phenyl.

The parameter m preferably is 0. The hydroxyalkyl of R is then preferably hydroxymethyl, 1-hydroxyethyl, 1-hydroxypropyl, 2-hydroxy-2-propyl, 1-hydroxybutyl, 2-hydroxy-2-butyl, 1-hydroxy-2-methylpropyl, 1-hydroxypentyl, 2-hydroxy-3-methyl-2-butyl, 3-hydroxy-3-methyl-2-butyl, 4-hydroxy-3-methyl-2-butyl, 2-hydroxy-2-pentyl, 3-hydroxy-2-pentyl, 4-hydroxy-2-pentyl, 1-hydroxyhexyl, 2-hydroxy-3-methyl-2-pentyl, 3-hydroxy-3-methyl-2-pentyl, 4-hydroxy-3-methyl-2-pentyl or 5-hydroxy-3-methyl-2-pentyl. R can also be 2-hydroxyethyl, 3-hydroxypropyl, 4-hydroxybutyl, 5-hydroxypentyl or 6-hydroxyhexyl.

If m is 1 and R is alkyl, R is preferably unbranched. If m is 1 and R is hydroxyalkyl or tetrahydropyran-2-yloxyalkyl, the alkyl in the alkyl part of R have straight chains. Thus, R preferably is ethyl, n-propyl, n-butyl, n-pentyl, n-hexyl, 2-hydroxyethyl, 3-hydroxypropyl, 4-hydroxybutyl, 5-hydroxypentyl, 6-hydroxyhexyl, 2-(tetrahydropyran-2-yloxy)-ethyl, 3-(tetrahydropyran-2-yloxy)-propyl, 4-(tetrahydropyran-2-yloxy)-butyl, 5-tetrahydropyran-2-yloxy)-pentyl or 6-(tetrahydropyran-2-yloxy)-hexyl, as well as isopropyl, isobutyl or tert.-butyl.

Preferred compounds of Formula I are those in which at least one of R, X, m or n has one of the above-given preferred meanings.

Preferred compounds of Formula I are those wherein:

(a) A is fluorophenyl or chlorophenyl;

(b) A is o- or p-fluorophenyl or o- or p-chlorophenyl;

(c) A is p-fluorophenyl or p-chlorophenyl, m is 0 and n is 0;

(d) A is p-fluorophenyl or p-chlorophenyl, m is 0, n is 0 and R is branched hydroxyalkyl of 1-4 carbon atoms;

(e) A is p-fluorophenyl or p-chlorophenyl, m is 1 and n is 0;

(f) A is p-fluorophenyl or p-chlorophenyl, m is 1, n is 0 and the alkyl of 2-6 carbon atoms in R is straight-chained, and (g) A is p-fluorophenyl or p-chlorophenyl, m is 1 and n is 1.

Compounds of Formula I are prepared according to known methods, such as described, e.g., in Houben-Weyl, Methoden der Organischen Chemie, George-Thieme-Verlag, Stuttgart; and Organic Reactions, John Wiley & Sons, Inc., New York, under the reaction conditions known and suitable for the desired reactions. Known variants, mentioned here in detail, can also be used.

Some of the starting materials for preparation of compounds of Formula I are known. Those which are new can be prepared according to known processes. The starting materials can also, if desired, be formed in situ and, without isolation from the reaction mixture, be immediately further reacted to give compounds of Formula I.

Compounds of Formula I are prepared by solvolysis, especially hydrolysis, of compounds of Formula II. In these, Q is a functionally-modified hydroxyl, e.g., a metal alcoholate or an acyloxy group.

Q is preferably a metal alcoholate OM in which M is an equivalent of a metal, e.g., an equivalent of an alkali metal or alkaline earth metal, especially of Li, Na, K, and Ca. Q can also be MgHal or CaHal, (Hal is Cl, Br or I). M can also be an equivalent of a heavy metal, e.g., of a metal of the first and second sub-Groups of the Periodic System, e.g., copper, silver, zinc, cadmium or mercury, as well as one of ZnHal or CdHal.

Compounds of Formula II (Q is OM) are preferably prepared in situ, e.g., under conditions for a Grignard reaction. They can be obtained by (a) reaction of a ketone of the formula $ArCOCH_3$ with a metal acetylide of the formula $MC\equiv CR$;

(b) by the reaction of a carbonyl compound of the formula $R'COR''$, wherein R' is H or alkyl of 1-4 carbon atoms and R'' alkyl of 1-5 carbon atoms, provided that R' and R'' together do not possess more than 5 carbon atoms, and wherein R' and R'' each are H is m is 0, with a metal acetylide of the formula $Ar[C(CH_3)(OH)]_m-C\equiv CM$;

(c) reaction of a ketone of the formula $Ar-CO-C\equiv CR$ with an organometallic compound of the formula $CH_3M$;

(d) reaction of a ketone of the formula $CH_3CO-C\equiv CR$ with an organometallic compound of the formula ArM, wherein Ar, R, M and m are as above; or (e) reaction of a ketone of the formula $Ar-C\equiv C-COR'$ or $Ar-C\equiv C-COR''$ with an organometallic compound of the formula MR'' or MR'.

These reactions expediently take place in an inert solvent at temperatures between about 0° and 100°, preferably at about 15°-50°, for reaction times of 10 minutes to 36 hours.

Inert solvents for this purpose include, e.g., ethers, such as diethyl, diisopropyl or diisobutyl ether, tetrahydrofuran (THF), dioxane, diethylene glycol diethyl or dibutyl ether; carbon tetrachloride; hydrocarbons, such as benzene, toluene or xylene possibly with oleic acid added; amides, such as formamide, acetamide, dimethyl formamide (DMF), diethyl formamide or dimethyl acetamide; acetals, such as methylal; dialkyl sulfoxides, such as dimethyl sulfoxide (DMSO) or diethyl sulfoxide; pyridine; and alcohols, such as methanol or ethanol. During the reaction, an inert gas, such as $N_2$ or argon, is possibly introduced into the system.

Instead of alkali metal acetylides, diamine complexes thereof, e.g., with ethylenediamine, preferably the lithium acetylideethylenediamine complex, can be used.

Advantageously, the metal acetylides can be formed in situ, e.g., using alkali metal and alkaline earth metal amides, hydrides or enolates, alkali or alkaline earth metals themselves or alkali organometallic compounds, such as phenyl or naphthyl sodium, potassium or lithium.

For reaction of carbonyl compounds with metal acetylides, alkaline catalysts, such as alkali metal or alkaline earth metal hydroxides, alcoholates or carbonates, e.g., NaOH, KOH, $NaOCH_3$, $KOCH_3$, $Na_2CO_3$ or $K_2CO_3$, can be used.

KOH is preferably used in ether in the presence of a little ethanol. Preferably, a slight excess of the acetylene compound and of KOH for the given reaction conditions, is used.

Reaction of carbonyl compounds with metal acetylides can also be carried out in liquid ammonia, possibly with the addition of one of the above inert solvents. Preferably, a mole ratio of 1:1 is used, possibly under pressure, e.g., 1 to 50 atmospheres, at temperatures between about $-77°$ and $30°$.

Compounds of Formula II in which Q is OM and M is an equivalent of a heavy metal, such as Ag or Cu, are also obtainable in situ by reaction of a carbonyl compound with a corresponding metal acetylide in the presence of a catalyst. Copper or silver acetylides obtainable, e.g., by reaction of a corresponding acetylene or a Grignard compound with a heavy metal salt, e.g., copper (I) chloride, can be used as catalysts.

Compounds of Formula II are obtainable under the above-given reaction conditions by reaction of a metal acetylide of Formula Ar—[C(CH$_3$)(OH)]$_m$—C≡CM, wherein Ar, M, Hal, m and n are as above, with a corresponding alkylene oxide, e.g., ethylene oxide, propylene oxide, 1,2- or 2,3-butylene oxide, 2,2-dimethylethylene oxide or 1,2,2-trimethylethylene oxide. The reaction is preferably carried out in THF at temperatures between about $-10°$ and $100°$, preferably between $-5°$ and $25°$. The alkylene oxide is employed in gaseous or liquid phase, possibly with cooling and/or increased pressure, e.g., 1.5–10 ats.

Carbonyl compounds of formula ArCO—C≡CR or CH$_3$CO—C≡CR are prepared, for example, by reaction of a carboxylic acid halogenide of the formula ArCOX or CH$_3$COX, in which X is Cl or Br, with an acetylide of the formula Li—C≡C—R, in, e.g., carbon tetrachloride. Carbonyl compounds of formula Ar—C≡C—CO—R' or Ar—C≡C—CO—R'' are obtainable analogously by reaction of a carboxylic acid halide of formulae R'—COX or R''COX with an acetylide of the formula Ar—C≡CLi. Carbonyl compounds of the formula Ar—COCH$_3$ are obtainable by the Friedel-Crafts acylation of compounds of formula Ar—H with, e.g., acetyl chloride.

Metal acetylides of formulae MC≡C—R or Ar—[C(CH$_3$)(OH)]$_m$—C≡C—M can be obtained according to known methods by reaction of a corresponding acetylene with an alkali metal, such as Li, Na or K; an alkali metal hydride, such as LiH, NaH or KH or an alkali metal amide, such as LiNH$_2$, NaNH$_2$ or KNH$_2$ in an anhydrous solvent, such as dioxane, DMSO, THF and/or liquid ammonia. Grignard compounds of the formula ArMgHal are obtainable from the corresponding halide and magnesium.

Q in compounds of Formula II can be present in the form of an acyloxy group, e.g., alkanoyloxy, wherein alkanoyl preferably is of up to 7 carbon atoms, e.g., acetyl or oenanthoyl; benzoyloxy; alkyl- or arylsulfonyloxy, wherein the alkyl preferably is of 1 to 6 and aryl preferably of 6 to 10 carbon atoms. The functionally-modified hydroxyl can also be alkoxy, wherein alkyl is preferably of up to 6 carbon atoms, aryloxy, wherein aryl preferably is of 6 to 10 carbon atoms, or aralkyloxy, wherein aralkyl preferably is of 7 to 11 carbon atoms. Q can also be Cl, Br or I, i.e., a hydrohalic acid ester group.

Compounds of Formula II wherein Q is alkanoyloxy, benzoyloxy, alkylsulfonyloxy or arylsulfonyloxy are obtainable by reaction of compounds of Formula II, wherein Q is Cl or Br with an alkali metal salt of the corresponding acid. By reaction of a halogen compound of Formula II (Q is Cl or Br) with an alkali metal alcoholate are obtained compounds of Formula II in which Q is an ether group. Reaction of compounds of Formula II (Q is Cl or Br) with potassium iodide in acetone gives compounds of Formula II in which Q is I.

Solvolysis of compounds of Formula II takes place in acidic, neutral or alkaline medium at temperatures between about $-20°$ and $300°$. As acidic catalysts are expediently used HCl, H$_2$SO$_4$ or acetic acid, as well as acid-reacting salts, such as ammonium chloride. Basic catalysts are, for example, sodium, potassium or calcium hydroxide and sodium or potassium carbonate. The solvent is preferably water; an alcohol, such as methanol or ethanol; an ether, such as THF or dioxane, an amide, such as DMF; a nitrile, such as acetonitrile; and/or a sulfone, such as tetramethylene sulfone. Solvent mixtures, especially mixtures which contain water, can be used.

If m is 1, in compounds of Formula II, two Q can be present simultaneously and can be the same or different. If Z in Q is tetrahydropyran-2-yloxy, the solvolysis can be done so that only Q which is not in Z is split off. It is also possible simultaneously to cleave solvolytically, especially hydrolytically, both Q, e.g., under somewhat more severe reaction conditions, such as higher temperature and/or longer reaction times. If Z in compounds of Formula II does not contain a tetrahydropyranyl group, then the solvolysis must be done so that all Q are split off.

Metal alcoholates of Formula II (Q is OM) preferred as starting materials are expediently not isolated but rather hydrolyzed in situ with a dilute acid, e.g., sulfuric acid or hydrochloric acid, or with aqueous ammonium chloride solution, preferably at temperatures between $0°$ and $30°$.

Compounds of Formula I, in which R is tetrahydropyran-2-yloxyalkyl, can, if desired, be cleaved hydrolytically, preferably by treatment with a dilute mineral acid, such as hydrochloric acid, in solvent mixtures, such as aqueous dioxane, at temperatures between $0°$ and $30°$.

Compounds of Formula I contain a center of asymmetry and are usually present in the form of a racemic mixture. The racemates can be separated into their optical antipodes by mechanical or chemical methods described in the literature.

Compounds of Formula I possess valuable pharmacological properties, particularly, anti-inflammatory, lipid level-depressing and thrombocyte aggregation-inhibiting activity, as well as analgesic and antipyretic activity. Anti-inflammatory activity can be demonstrated in rats by the adjuvant arthritis test according to Newbould, Brit. J. Pharmacol., Volume 21, (1963), pages 127–136. Of lipid-depressing activity, cholesterol level-depressing activity is detectable according to Levine et al., Automation in Analytical Chemistry, Technicon Symposium 1967, Mediad, New York, pages 25–28, and triglyceride-depressing activity according to Noble and Campbell, Clin. Chem., Volume 16 (1970) pages 166–170. Thrombocyte aggregation-inhibiting, analgesic and antipyretic activity can be ascertained according to conventional methods.

Compounds of Formula I can be used as pharmaceuticals in human and veterinary medicine.

Compounds of Formula I can be used for the preparation of pharmaceutical preparations by formulation into a suitable dosage form together with at least one carrier or adjuvant material and possibly together with one or more further active materials. The thus-obtained compositions can be used as pharmaceuticals in human and veterinary medicine.

Carrier substances include organic or inorganic materials which are suitable for enteral, e.g., oral, parenteral or topical administration and which do not react with the new compounds, for example, water, vegetable oils, benzyl alcohols, polyethylene glycols, gelatine, carbohydrates, such as lactose or starch, magnesium stearate, talc, and vaseline. Forms for enteral administration are particularly tablets, dragees, capsules, syrups, juices, drops or suppositories; for parenteral administration, solutions, preferably oily or aqueous solutions, and suspensions, emulsions or implants; for topical use, salves, creams or powders.

The new compounds can also be lyophilized and the lyophilizates obtained used, e.g., for the preparation of injectable preparations. The stated compositions can be sterilized and/or contain adjuvants, such as lubricants, preservatives, stabilizers and/or wetting agents, emulsifiers, salts for influencing osmotic pressure, buffers, coloring, flavoring and/or aromatic materials. If desired, they can contain one or more additional active materials.

The substances of the invention are administered as for known antiphlogistics commercially available, e.g., Indometacine preferably in dosages between about 5 and 500 mg., especially between 10 and 250 mg. per dosage unit. The daily dosage preferably is between about 0.1 and 10 mg./kg. of body weight.

The dose for a particular patient depends, however, on the most varied factors, for example, effectiveness of the special compound employed, age, body weight, general state of health, sex, food, time and route of administration, rate of excretion, pharmaceutical combination and severity of the disease for which the therapy is applied. Oral administration is preferred.

Each of the compounds of Formula I in the following Examples is especially suitable for the preparation of pharmaceutical compositions.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

In following Examples, "usual work up" means: If necessary, water is added to the reaction mixture, which is extracted with an organic solvent, such as benzene, chloroform or dichloromethane. The organic phased is separated off, dried over sodium sulfate, filtered, evaporated and purified by chromatography and/or crystallization.

EXAMPLE 1

A Grignard solution is prepared from 5.1 g. of magnesium turnings and 12.5 ml. of ethyl bromide in 100 ml. of ether and to this is added dropwise, with stirring, 19.6 g. of 4-(4-fluorophenyl)phenylacetylene, obtainable by reaction of 4-fluorobiphenyl with acetyl chloride, chlorination with PCl$_5$ at 70° C. and subsequent dehydrochlorination with potassium tert.-butylate in tert.-butanol, in 400 ml. of ether and 25 ml. of THF. The mixture is stirred for one hour at 20° C. and added dropwise to a solution of 11.6 g. of acetone in 36 ml. of ether and stirred for an hour more at 20° C. Subsequently, magnesium alcoholate formed of the formula p-F-C$_6$H$_4$—p—C$_6$H$_4$—C≡C-C(CH$_3$)$_2$ —O—MgBr is hydrolyzed in situ by dropwise addition of 300 ml. of 2 N hydrochloric acid with stirring (15 minutes at 20° C.). After usual work up, there is obtained 4-(4'-fluoro-4-biphenylyl)-2-methyl-3-butyn-2-ol, m.p. 118° C.

EXAMPLES 2 to 7

Analogously to Example 1 are obtained with formaldehyde, acetaldehyde, propionaldehyde, butyraldehyde, isobutyraldehyde or butanone:
2. 3-(4'-fluoro-4-biphenylyl)-2-propyn-1-ol, m.p. 131° C.
3. 4-(4'-fluoro-4-biphenylyl)-3-butyn-2-ol.
4. 5-(4'-fluoro-4-biphenylyl)-4-pentyn-3-ol.
5. 6-(4'-fluoro-4-biphenylyl)-5-hexyn-4-ol.
6. 5-(4'-fluoro-4-biphenylyl)-2-methyl-4-pentyn-3-ol, m.p. 92°-93° C.
7. 5-(4'-fluoro-4-biphenylyl)-3-methyl-4-pentyn-3-ol, m.p. 93° C.

EXAMPLES 8 to 94

Analogously to Example 1, are obtained, using the corresponding arylacetylenes:
8. 3-(2'-fluoro-4-biphenylyl)-2-propyn-1-ol.
9. 4-(2'-fluoro-4-biphenylyl)-3-butyn-2-ol.
10. 5-(2'-fluoro-4-biphenylyl)-4-pentyn-3-ol.
11. 6-(2'-fluoro-4-biphenylyl)-5-hexyn-4-ol.
12. 5-(2'-fluoro-4-biphenylyl)-2-methyl-4-pentyn-3-ol.
13. 4-(2'-fluoro-4-biphenylyl)-2-methyl-3-butyn-2-ol.
14. 5-(2'-fluoro-4-biphenylyl)-3-methyl-4-pentyn-3-ol.
15. 3-(3'-fluoro-4-biphenylyl)-2-propynol.
16. 4-(3'-fluoro-4-biphenylyl)-2-methyl-3-butyn-2-ol.
17. 5-(3'-fluoro-4-biphenylyl)-3-methyl-4-pentyn-3-ol.
18. 3-(2'-chloro-4-biphenylyl)-2-propyn-1-ol.
19. 4-(2'-chloro-4-biphenylyl)-3-butyn-2-ol.
20. 5-(2'-chloro-4-biphenylyl)-4-pentyn-3-ol.
21. 6-(2'-chloro-4-bipehnylyl)-5-hexyn-4-ol.
22. 5-(2'-chloro-4-biphenylyl)-2-methyl-4-pentyn-3-ol.
23. 4-(2'-chloro-4-biphenylyl)-2-methyl-3-butyn-2-ol.
24. 5-(2'-chloro-4-biphenylyl)-3-methyl-4-pentyn-3-ol.
25. 3-(3'-chloro-4-biphenylyl)-2-propyn-1-ol.
26. 4-(3'-chloro-4-biphenylyl)-3-butyn-2-ol.
27. 5-(3'-chloro-4-biphenylyl)-4-pentyn-3-ol.
28. 6-(3'-chloro-4-biphenylyl)-5-hexyn-4-ol.
29. 5-(3'-chloro-4-biphenylyl)-2-methyl-4-pentyn-3-ol.
30. 4-(3'-chloro-4-biphenylyl)-2-methyl-3-butyn-2-ol.
31. 5-(3'-chloro-4-biphenylyl)-3-methyl-4-pentyn-3-ol.
32. 3-(4'-chloro-4-biphenylyl)-2-propyn-1-ol.
33. 4-(4'-chloro-4-biphenylyl)-3-butyn-2-ol.
34. 5-(4'-chloro-4-biphenylyl)-4-pentyn-3-ol.
35. 6-(4'-chloro-4-biphenylyl)-5-hexyn-4-ol.
36. 5-(4'-chloro-4-biphenylyl)-2-methyl-4-pentyn-3-ol.
37. 4-(4'-chloro-4-biphenylyl)-2-methyl-3-butyn-2-ol, m.p. 136°-137°.
38. 5-(4'-chloro-4-biphenylyl)-3-methyl-4-pentyn-3-ol.
39. 3-(2'-bromo-4-biphenylyl)-2-propynol.
40. 4-(2'-bromo-4-biphenylyl)-2-methyl-3-butyn-2-ol.
41. 5-(2'-bromo-4-biphenylyl)-3-methyl-4-pentyn-3-ol.
42. 3-(3'-bromo-4-biphenylyl)-2-propynol.
43. 4-(3'-bromo-4-biphenylyl)-2-methyl-3-butyn-2-ol.
44. 5-(3'-bromo-4-biphenylyl)-3-methyl-4-pentyn-3-ol.
45. 3-(4'-bromo-4-biphenylyl)-2-propynol.
46. 4-(4'-bromo-4-biphenylyl)-2-methyl-3-butyn-2-ol.
47. 5-(4'-bromo-4-biphenylyl)-3-methyl-4-pentyn-3-ol.

48. 3-(4-o-fluorophenoxyphenyl)-2-propyn-1-ol.
49. 4-(4-o-fluorophenoxyphenyl)-3-butyn-2-ol.
50. 5-(4-o-fluorophenoxyphenyl)-4-pentyn-3-ol.
51. 6-(4-o-fluorophenoxyphenyl)-5-hexyn-4-ol.
52. 5-(4-o-fluorophenoxyphenyl)-2-methyl-4-pentyn-3-ol.
53. 4-(4-o-fluorophenoxyphenyl)-2-methyl-3-butyn-2-ol.
54. 5-(4-o-fluorophenoxyphenyl)-3-methyl-4-pentyn-3-ol.
55. 3-(4-m-fluorophenoxyphenyl)-2-propynol.
56. 4-(4-m-fluorophenoxyphenyl)-2-methyl-3-butyn-2-ol.
57. 5-(4-m-fluorophenoxyphenyl)-3-methyl-4-pentyn-3-ol.
58. 3-(4-p-fluorophenoxyphenyl)-2-propyn-1-ol.
59. 4-(4-p-fluorophenoxyphenyl)-3-butyn-2-ol.
60. 5-(4-p-fluorophenoxyphenyl)-4-pentyn-3-ol.
61. 6-(4-p-fluorophenoxyphenyl)-5-hexyn-4-ol.
62. 5-(4-p-fluorophenoxyphenyl)-2-methyl-4-pentyn-3-ol.
63. 4-(4-p-fluorophenoxyphenyl)-2-methyl-3-butyn-2-ol.
64. 5-(4-p-fluorophenoxyphenyl)-3-methyl-4-pentyn-3-ol.
65. 3-(4-o-chlorophenoxyphenyl)-2-propyn-1-ol.
66. 4-(4-o-chlorophenoxyphenyl)-3-butyn-2-ol.
67. 5-(4-o-chlorophenoxyphenyl)-4-pentyn-3-ol.
68. 6-(4-o-chlorophenoxyphenyl)-5-hexyn-4-ol.
69. 5-(4-o-chlorophenoxyphenyl)-2-methyl-4-pentyn-3-ol.
70. 4-(4-o-chlorophenoxyphenyl)-2-methyl-3-butyn-2-ol.
71. 5-(4-o-chlorophenoxyphenyl)-3-methyl-4-pentyn-3-ol.
72. 3-(4-m-chlorophenoxyphenyl)-2-propyn-1-ol.
73. 4-(4-m-chlorophenoxyphenyl)-3-butyn-2-ol.
74. 5-(4-m-chlorophenoxyphenyl)-4-pentyn-3-ol.
75. 6-(4-m-chlorophenoxyphenyl)-5-hexyn-4-ol.
76. 5-(4-m-chlorophenoxyphenyl)-2-methyl-4-pentyn-3-ol.
77. 4-(4-m-chlorophenoxyphenyl)-2-methyl-3-butyn-2ol.
78. 5-(4-m-chlorophenoxyphenyl)-3-methyl-4-pentyn-3-ol.
79. 3-(4-p-chlorophenoxyphenyl)-2-propyn-1-ol.
80. 4-(4-p-chlorophenoxyphenyl)-3-butyn-2-ol.
81. 5-(4-p-chlorophenoxyphenyl)-4-pentyn-3-ol.
82. 6-(4-p-chlorophenoxyphenyl)-5-hexyn-4-ol.
83. 5-(4-chlorophenoxyphenyl)-2-methyl-4-pentyn-3-ol.
84. 4-(4-p-chlorophenoxyphenyl)-2-methyl-3-butyn-2-ol.
85. 5-(4-p-chlorophenoxyphenyl)-3-methyl-4-pentyn-3-ol.
86. 3-(4-o-bromophenoxyphenyl)-2-propynol.
87. 4-(4-o-bromophenoxyphenyl)-2-methyl-3-butyn-2-ol.
88. 5-(4-o-bromophenoxyphenyl)-3-methyl-4-pentyn-3-ol.
89. 3-(4-m-bromophenoxyphenyl)-2-propynol.
90. 4-(4-m-bromophenoxyphenyl)-2-methyl-3-butyn-2-ol.
91. 5-(4-m-bromophenoxyphenyl)-3-methyl-4-pentyn-3-ol.
92. 3-(4-p-bromophenoxyphenyl)-2-propynol.
93. 4-(4-p-bromophenoxyphenyl)-2-methyl-3-butyn-2-ol.
94. 5-(4-p-bromophenoxyphenyl)-3-mehtyl-4-pentyn-3-ol.

EXAMPLE 95

15.4 g. of 4-(tetrahydropyran-2-yloxy)-1-butyne, obtainable from 4-hydroxy-1-butyne and dihydropyran, are converted into 4-(tetrahydropyran-2-yloxy)-1-butyne-1 magnesium bromide with ethyl magnesium bromide solution prepared from 6.5 ml. of ethyl bromide and 2.69 g. of magnesium in 95 ml. of absolute ether. This product is stirred for 1 hour at 20° with 10 g. of 4-(4-fluorophenyl)-acetophenone, dissolved in 95 ml. of absolute THF. This mixture contains 2-(4'-fluoro-4-biphenylyl)-6-(tetrahydropyran-2-yloxy)-3-hexyn-2-oxy-magnesium bromide. To this is added 100 ml. of 10% NH4Cl solution. The mixture is stirred for 5 minutes at 20°. After the usual work up, there is obtainted 2-(4'-fluoro-4-biphenylyl)-6-(tetrahydropyran-2-yloxy)-3-hexyn-2-ol as an oil; $n_D^{20}$=1.5578.

EXAMPLES 96 to 124

Analogously to Example 95, are obtained from the corresponding ketones and corresponding alkynyl magnesium bromides:
96. 2-(4'-fluoro-4-biphenylyl)-3-hexyn-2-ol.
97. 2-(4'-fluoro-4-biphenylyl)-3-heptyn-2-ol, m.p. 71°.
98. 2-(4'-fluoro-4-biphenylyl)-3-octyn-2-ol, m.p. 62°.
99. 2-(4'-chloro-4-biphenylyl)-3-hexyn-2-ol.
100. 2-(4'-chloro-4-biphenylyl)-3-heptyn-2-ol.
101. 2-(4'-chloro-4-biphenylyl)-3-octyn-2-ol, m.p. 59°.
102. 2-(4-p-fluorophenoxyphenyl)-3-hexyn-2-ol.
103. 2-(4-p-fluorophenoxyphenyl)-3-heptyn-2-ol.
104. 2-(4-p-fluorophenoxyphenyl)-3-octyn-2-ol.
105. 2-(4-p-chlorophenoxyphenyl)-3-hexyn-2-ol.
106. 2-(4-p-chlorophenoxyphenyl)-3-heptyn-2-ol.
107. 2-(4-p-chlorophenoxyphenyl)-3-octyn-2-ol, $n_D^{20}$ 1.559.
108. 2-(4'-fluoro-4-biphenylyl)-7-(tetrahydropyran-2-yloxy)-3-heptyn-2-ol.
109. 2-(4'-fluoro-4-biphenylyl)-8-(tetrahydropyran-2-yloxy)-3-octyn-2-ol.
110. 2-(2'-chloro-4-biphenylyl)-6-(tetrahydropyran-2-yloxy)-3-hexyn-2-ol.
111. 2-(4'-chloro-4-biphenylyl)-6-(tetrahydropyran-2-yloxy)-3-hexyn-2-ol, $n_D^{20}$ 1.5788.
112. 2-(4'-chloro-4-biphenylyl)-7-(tetrahydropyran-2-yloxy)-3-heptyn-2-ol.
113. 2-(4'-chloro-4-biphenylyl)-8(tetrahydropyran-2-yloxy)-3-octyn-2-ol.
114. 2-(4'-bromo-4-biphenylyl)-6-(tetrahydropyran-2-yloxy)-3-hexyn-2-ol.
115. 2-(4-o-fluorophenoxyphenyl)-6-tetrahydropyran-2-yloxy)-3-hexyn-2-ol.
116. 2-(4-m-fluorophenoxyphenyl)-6-(tetrahydropyran-2-yloxy)-3-hexyn-2-ol.
117. 2-(4-fluorophenoxyphenyl)-6-(tetrahydropyran-2-yloxy)-3-hexyn-2-ol.
118. 2-(4-p-fluorophenoxyphenyl)-7(tetrahydropyran-2-yloxy)-3-heptyn-2-ol.
119. 2-(4-p-fluorophenoxyphenyl)-8-(tetrahydropyran-2-yloxy)-3-octyn-2-ol.
120. 2-(4-o-chlorophenoxyphenyl)-6-(tetrahydropyran-2-yloxy)-3-hexyn-2-ol.
121. 2-(4-p-chlorophenoxyphenyl)-6-(tetrahydropyran-2-yloxy)-3-hexyn-2-ol, $n_D^{20}$ 1.557.
122. 2-(4-p-chlorophenoxyphenyl)-7-(tetrahydropyran-2-yloxy)-3-heptyn-2-ol.

123. 2-(4-p-chlorophenoxyphenyl)-8-(tetrahydropyran-2-yloxy)-3-octyn-2-ol.
124. 2-(4-p-bromophenoxyphenyl)-6-(tetrahydropyran-2-yloxy)-3-hexyn-2-ol.

EXAMPLE 125

To 38.5 g. of 2-(4'-chloro-4-biphenylyl)-6-(tetrahydropyran-2-yloxy)-3-hexyn-2-ol in 250 ml. of dioxane, is added dropwise with ice cooling, 100 ml. of 1 N HCl. The resulting mixture is stirred 12 hours more at 0°. After the usual work up, 2-(4'-chloro-4-biphenylyl)-3-hexyn-2,6-diol, m.p. 105°, is obtained.

EXAMPLES 126 to 144

Analogously to Example 125, are obtained by hydrolysis of the corresponding tetrahydropyranyl ethers:
126. 2-(2'-fluoro-4-biphenylyl)-3-hexyn-2,6-diol.
127. 2-(3'-fluoro-4-biphenylyl)-3-hexyn-2,6-diol.
128. 2-(4'-fluoro-4-biphenylyl)-3-hexyn-2,6-diol.
129. 2-(4'-fluoro-4-biphenylyl)-3-heptyn-2,7-diol.
130. 2-(4'-fluoro-4-biphenylyl)-3-octyn-2,8-diol.
131. 2-(2'-chloro-4-biphenylyl)-3-hexyn-2,6-diol.
132. 2-(4'-chloro-4-biphenylyl)-3-heptyn-2,7-diol.
133. 2-(4'-chloro-4-biphenylyl)-3-octyn-2,8-diol.
134. 2-(4'-bromo-4-biphenylyl)-3-hexyn-2,6-diol.
135. 2-(4-o-fluorophenoxyphenyl)-3-hexyn-2,6-diol.
136. 2-(4-m-fluoropheoxyphenyl)-3-hexyn-2,6-diol.
137. 2-(4-p-fluorophenoxyphenyl)-3-hexyn-2,6-diol.
138. 2-(4-p-fluorophenoxyphenyl)-3-heptyn-2,7-diol.
139. 2-(4-p-fluorophenoxyphenyl)-3-octyn-2,8-diol.
140. 2-(4-o-chlorophenoxyphenyl)-3-hexyn-2,6-diol.
141. 2-(4-p-chlorophenoxyphenyl)-3-hexyn-2,6-diol.
142. 2-(4-p-chlorophenoxyphenyl)-3-heptyn-2,7-diol.
143. 2-(4-p-chlorophenoxyphenyl)-3-octyn-2,8-diol.
144. 2-(4-p-bromophenoxyphenyl)-3-hexyn-2,6-diol.

EXAMPLE 145

19.6 g. of 4-ethynyl-4'-fluorobiphenyl in 200 ml. THF is converted with an excess of ethyl magnesium bromide to the Grignard compound, to which is added 100 ml. of THF and then a solution of 5 g. of ethylene oxide in 10 ml. of THF. After subsidance of the exothermic reaction, the mixture is heated under reflux for 1 hour. 4-(4'-Fluoro-4-biphenylyl)-3-butyn-1-oxymagnesium bromide is thereby formed in situ. To this is added 150 ml. of 1 N hydrochloric acid. After stirring for 20 minutes at 20° and the usual work up, 4-(4'-fluoro-4-biphenylyl)-3-butyn-1-ol, m.p. 134°, is obtained.

EXAMPLES 146 to 186

Analogously to Example 145, are obtained from the corresponding arylacetylenes and corresponding alkylene oxides:
146. 4-(2'-fluoro-4-biphenylyl)-3-butyn-1-ol.
147. 4-(3'-fluoro-4-biphenylyl)-3-butyn-1-ol.
148. 4-(2'-chloro-4-biphenylyl)-3-butyn-1-ol.
149. 4-(3'-chloro-4-biphenylyl)-3-butyn-1-ol.
150. 4-(4'-chloro-4-biphenylyl)-3-butyn-1-ol, m.p. 141°–142°.
151. 4-(4'-bromo-4-biphenylyl)-3-butyn-1-ol.
152. 5-(2'-fluoro-4-biphenylyl)-3-methyl-4-pentyn-2-ol.
153. 5-(3'-fluoro-4-biphenylyl)-3-methyl-4-pentyn-2-ol.
154. 5-(4'-fluoro-4-biphenylyl)-3-methyl-4-pentyn-2-ol.
155. 5-(2'-chloro-4-biphenylyl)-3-methyl-4-pentyn-2-ol.
156. 5-(3'-chloro-4-biphenylyl)-3-methyl-4-pentyn-2-ol.
157. 5-(4'-chloro-4-biphenylyl)-3-methyl-4-pentyn-2-ol.
158. 5-(4'-bromo-4-biphenylyl)-3-methyl-4-pentyn-2-ol.
159. 5-(2'-fluoro-4-biphenylyl)-2,3-dimethyl-4-pentyn-2-ol.
160. 5-(3'-fluoro-4-biphenylyl)-2,3-dimethyl-4-pentyn-2-ol.
161. 5-(4'-fluoro-4-biphenylyl)-2,3-dimethyl-4-pentyn-2-ol.
162. 5-(2'-chloro-4-biphenylyl)-2,3-dimethyl-4-pentyn-2-ol.
163. 5-(3'-chloro-4-biphenylyl)-2,3-dimethyl-4-pentyn-2-ol.
164. 5-(4'-chloro-4-biphenylyl)-2,3-dimethyl-4-pentyn-2-ol.
165. 5-(4'-bromo-4-biphenylyl)-2,3-dimethyl-4-pentyn-2-ol.
166. 4-(4-o-fluorophenoxyphenyl)-3-butyn-1-ol.
167. 4-(4-m-fluorophenoxyphenyl)-3-butyn-1-ol.
168. 4-(4-p-fluorophenoxyphenyl)-3-butyn-1-ol.
169. 4-(4-o-chlorophenoxyphenyl)-3-butyn-1-ol.
170. 4-(4-m-chlorophenoxyphenyl)-3-butyn-1-ol.
171. 4-(4-p-chlorophenoxyphenyl)-3-butyn-1-ol.
172. 4-(4-p-bromophenoxyphenyl)-3-butyn-1-ol.
173. 5-(4-o-fluorophenoxyphenyl)-3-methyl-4-pentyn-2-ol.
174. 5-(4-m-fluorophenoxyphenyl)-3-methyl-4-pentyn-2-ol.
175. 5-(4-p-fluorophenoxyphenyl)-3-methyl-4-pentyn-2-ol.
176. 5-(4-o-chlorophenoxyphenyl)-3-methyl-4-pentyn-2-ol.
177. 5-(4-m-chlorophenoxyphenyl)-3-methyl-4-pentyn-2-ol.
178. 5-(4-p-chlorophenoxyphenyl)-3-methyl-4-pentyn-2-ol.
179. 5-(4-p-bromophenoxyphenyl)-3-methyl-4-pentyn-2-ol.
180. 5-(4-o-fluorophenoxyphenyl)-2,3-dimethyl-4-pentyn-2-ol.
181. 5-(4-m-fluorophenoxyphenyl)-2,3-dimethyl-4-pentyn-2-ol.
182. 5-(4-p-fluorophenoxyphenyl)-2,3-dimethyl-4-pentyn-2-ol.
183. 5-(4-o-chlorophenxoyphenyl)-2,3-dimethyl-4-pentyn-2-ol.
184. 5-(4-m-chlorophenoxyphenyl)-2,3-dimentyl-4-pentyn-2-ol.
185. 5-(4-p-chlorophenoxyphenyl)-2,3-dimethyl-4-pentyn-2-ol.
186. 5-(4-p-bromophenoxyphenyl)-2,3-dimethyl-4-pentyn-2-ol.

EXAMPLE 187

2.43 g. of sodium hydride in added portionwise to a solution of 8.2 g. of 1-hexyne in 30 ml. of dry THF and then, under a stream of nitrogen, a solution of 21.4 g. of 4'-fluoro-4-acetylbiphenyl, preparable from 4-fluorobiphenyl and acetyl chloride in the presence of AlCl₃, in 60 ml. of THF is added thereto. The reaction mixture contains sodium 2-(4'-fluoro-4-biphenylyl)-3-octyn-2-olate. It is hydrolyzed with an aqueous 15% ammonium chloride solution and worked up as usual. There is obtained 2-(4'-fluoro-4-biphenylyl)-3-octyn-2-ol; m.p. 62°.

EXAMPLE 188

214 g. of 4'-fluoro-4-acetylbiphenyl is dropped, within 3 hours, into a solution of 1-hexyne sodium prepared from 25 g. of sodium and 104 g. of 1-n-hexyne in 600 ml. of liquid ammonia. The mixture is stirred for 150 minutes at −35°. 65 g. ammonium chloride are then added to the solution which contains sodium 2-(4'-fluoro-4-biphenylyl)-3-octyn-2-olate and ammonia is evaporated off. After the usual work up, 2-(4'-fluoro-4-biphenylyl)-3-octyn-2-ol; m.p. 62° is obtained.

EXAMPLE 189

8.34 g. of lithium is added at −70°, over three hours, to 900 ml. of liquid ammonia containing 82 g. of 1-hexyne. When the blue color has disappeared, 214 g. of 4'-fluoro-4-acetylbiphenylyl in 200 ml. of ether are added thereto over one hour. The solution contains lithium 2-(4'-fluoro-4-biphenylyl)-3-octyn-2-olate. Subsequently, the ammonia is allowed to evaporate at +25° and simultaneously ether is added at a rate such that the volume of the mixture remains constant. After removal of ammonia, the mixture is allowed to stand for 12 hours at 20°. Thereafter, it is hydrolyzed with 150 ml. water and worked up as usual, to give 2-(4'-fluoro-4-biphenylyl)-3-octyn-2-ol; m.p. 62°.

EXAMPLE 190

A solution of 28 g. of 1-(4'-fluoro-4-biphenylyl)-2-heptyn-1-one, preparable from 1-(4'-fluoro-4-biphenylyl)-2-heptyn-1-ol by oxidation with chromium trioxide/sulfuric acid in water/acetone, in 100 ml. of absolute ether is added to a Grignard solution, cooled to 0°, prepared from 5.3 g. of magnesium and 31.2 g. of methyl iodide in 200 ml. of diethyl ether. The stirred solution which contains 2-(4'-fluoro-4-biphenylyl)-3-octyn-2-yloxy-magnesium iodide, is allowed to come to 20° and is hydrolyzed with 150 ml. of 12% aqueous ammonium chloride solution for 20 minutes. After the usual work up, 2-(4'-fluoro-4-biphenylyl)-3-octyn-2-ol; m.p. 62°, is obtained.

EXAMPLE 191

A solution of 12.4 g. of 3octyn-2-one in 100 ml. of diethyl ether at 0° is added to a solution of 4'-fluorobiphenylyl-4 magnesium bromide, preparable by nitration of 4-fluorobiphenyl, reduction of 4'-fluoro-4-nitrobiphenyl to the amine, conversion thereof to 4'-fluoro-4-bromobiphenyl according to Sandmeyer and subsequent reaction of 25.1 g. of this compound with magnesium, in 400 ml. diethyl ether. The stirred solution is allowed to come to 20° and stirred for 2 hours more at 20°. Hydrolysis of 2-(4'-fluoro-4-biphenylyl)-3-octyn-3-yloxy magnesium bromide is by addition of 10% aqueous ammonium chloride solution and the product is isolated by the usual work up. The product is 2-(4'-fluoro-4-biphenylyl)-3-octyn-2-ol; m.p. 62°.

The following Examples relate to pharmaceutical compositions which contain compounds of the Formula I:

EXAMPLE A: TABLETS

A mixture of 1 kg. of 4-(4'-fluoro-4-biphenylyl)-2-methyl-3-butyn-2-ol, 4 kg. of lactose, 1.2 kg. of potato starch, 0.2 kg. of talc and 0.1 kg. of magnesium stearate is pressed in the usual way into tablets so that each tablet contains 100 mg. of active material.

EXAMPLE B: DRAGEES

Analogously to Example A, tablets are pressed which are subsequently coated in the usual way with a coating of saccharose, potato starch, talc, tragacanth and coloring material.

EXAMPLE C: CAPSULES 5 kg. of 4-(4'-fluoro-4-biphenylyl)-2-methyl-3-butyn-2-ol are charged, in the usual way, into hard gelatin capsules so that each capsule contains 250 mg. of active material.

Tablets, dragees and capsules, which contain one or more of the other active materials of the Formula I, are obtainable analogously.

The preceding examples can be repeated with similar success by substituting the generically or specifically described reactants and/or operating conditions of this invention for those used in the proceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An alkynol of the formula

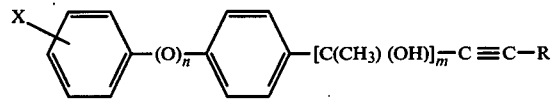

wherein X is F, Cl or Br; n is 0 or 1; m is 0 or 1 and R, when m is 0, is hydroxyalkyl of 1–6 carbon atoms, or, when m is 1, is alkyl or straight-chain tetrahydropyran-2-yloxyalkyl, each alkyl being of 2–6 carbon atoms.

2. 3-(4'-Fluoro-4-biphenylyl)-2-propyn-1-ol, a compound of claim 1.

3. 4-(4'-Fluoro-4-biphenylyl)-3-butyn-1-ol, a compound of claim 1.

4. 4-(4'-Fluoro-4biphenylyl)-2-methyl-3-butyn-2-ol, a compound of claim 1.

5. 5-(4'-Fluoro-4-biphenylyl)-2-methyl-4-pentyn-3-ol, a compound of claim 1.

6. 5-(4'-Fluoro-4-biphenylyl)-3-methyl-4-pentyn-3-ol, a compound of claim 1.

7. 2-(4'-Fluoro-4-biphenylyl)-6-(tetrahydropyran-2-yloxy)-3-hexyn-2-ol, a compound of claim 1.

8. 2-(4'-Fluoro-4-biphenylyl)-3-heptyn-2-ol, a compound of claim 1.

9. 2-(4'-Fluoro-4-biphenylyl)-3octyn-2-ol, a compound of claim 1.

10. 4-(4'-Chloro-4-biphenylyl)-3-butyn-1-ol, a compound of claim 1.

11. 4-(4'-Chloro-4-biphenylyl)-2-methyl-3-butyn-2-ol, a compound of claim 1.

12. 2-(4'-Chloro-4-biphenylyl)-6-(tetrahydropyran-2-yloxy)-3-hexyn-2-ol, a compound of claim 1.

13. 2-(4'-Chloro-4-biphenylyl)-3-octyn-2-ol, a compound of claim 1.

14. 2-(4-p-Chlorophenoxyphenyl)-3-octyn-2-ol, a compound of claim 1.

15. 2-(4-p-Chlorophenoxyphenyl)-6-(tetrahydropyran-2-yloxy)-3-hexyn-2-ol, a compound of claim 1.

16. A pharmaceutical composition comprising an amount of a compound of claim 1 effective to lower the serum triglyceride level, in admixture with a pharmaceutically acceptable carrier.

17. A method of treating inflammation in an animal comprising administering to the afflicted animal an amount of a compound of claim 1 effective to lower the serum triglyceride level.

* * * * *